US006582912B1

(12) United States Patent
Rousseau et al.

(10) Patent No.: US 6,582,912 B1
(45) Date of Patent: Jun. 24, 2003

(54) DEVICE, METHOD AND APPARATUS FOR IMPLEMENTING THE METHOD, FOR DOSING AT LEAST A PARTICULAR CONSTITUENT IN A PRODUCT SAMPLE

(75) Inventors: Alain Rousseau, Paris (FR); Michel Canton, Cassis (FR)

(73) Assignee: Stago International, Asnieres (FR)

( * ) Notice: Subject to any disclaimer, the term of this patent is extended or adjusted under 35 U.S.C. 154(b) by 0 days.

(21) Appl. No.: 09/582,610

(22) PCT Filed: Dec. 7, 1998

(86) PCT No.: PCT/FR98/02639

§ 371 (c)(1), (2), (4) Date: Aug. 14, 2000

(87) PCT Pub. No.: WO99/35483

PCT Pub. Date: Jul. 15, 1999

(30) Foreign Application Priority Data

Dec. 31, 1997 (FR) ........................................... 97 16787

(51) Int. Cl.[7] ...................... G01N 33/53; G01N 33/543; G01N 33/00; C12M 3/00

(52) U.S. Cl. ............................... 435/6; 435/4; 435/7.1; 435/7.92; 435/287.1; 435/287.2; 435/287.3; 435/288.2; 435/288.4; 435/288.5; 435/288.7; 435/808; 422/63; 422/64; 422/68.1; 422/82.05; 422/102; 436/164; 436/172; 436/174; 436/518; 436/524; 436/528; 436/805; 436/807

(58) Field of Search ....................... 435/4, 6, 7.1, 7.92, 435/287.1–287.3, 287.6, 288.7, 808; 436/518, 524, 528, 164, 172, 174, 805, 807; 422/63, 64, 68.1, 82.05, 102

(56) References Cited

U.S. PATENT DOCUMENTS

| | | | | |
|---|---|---|---|---|
| 4,652,137 A | * | 3/1987 | Calzi | 356/414 |
| 4,756,883 A | * | 7/1988 | Romanauskas | 356/246 |
| 5,470,710 A | * | 11/1995 | Weiss et al. | 435/6 |

FOREIGN PATENT DOCUMENTS

EP 0 339 277 A1 * 11/1989

* cited by examiner

*Primary Examiner*—Long V. Le
*Assistant Examiner*—Kartic Padmanabhan
(74) *Attorney, Agent, or Firm*—Levine & Mandelbaum

(57) ABSTRACT

A device for dosing at least a particular constituent in a product sample has a receptacle and a cover assembled to form a closed container having a vertical axis. The receptacle and cover bear coaxial cylindrical walls defining concentric annular chambers inside the container, the walls separating chambers each having an opening, the cover and the container being rotatable relative to each other about the vertical axis, said openings being placed in a predetermined manner so that by relative displacement of the walls, the openings are positioned in a straight line or offset to communicate, or isolate said successive chambers. A method for using such a device and an apparatus for implementing said method are disclosed.

32 Claims, 3 Drawing Sheets

DEVICE, METHOD AND APPARATUS FOR IMPLEMENTING THE METHOD, FOR DOSING AT LEAST A PARTICULAR CONSTITUENT IN A PRODUCT SAMPLE

This application is the US National Stage Filing of PCR/FR98/02639 field on Dec. 7, 1998.

BACKGROUND OF THE INVENTION

The present invention relates to a device intended for the qualitative or quantitative dosing of at least one particular component in a product-sample, preferably making it possible to implement immunological dosing, as well as to a process and a kit which are intended for implementing the device.

Numerous methods have been developed for identifying, detecting or quantifying analytes in chemical or biological samples.

These methods are mostly based on the formation of complexes by affinity reaction between members of a specific binding pair.

These reactions, of ligand/receptor type, result for example from interactions between an antigen and a specific antibody, from hybridization between two complementary nucleic acid sequences or from a phenomenon of recognition between the binding site of a protein, for example an enzyme, hormone or other biological entity, and its ligand, substrate or receptor.

The formation of an affinity complex makes it possible to reveal the presence of the sought-after analyte in the sample. This analyte may possibly be quantified, if it is possible to separate the complexed forms from those remaining in the free state, or to measure the degree of occupancy of the specific ligands of the analyte.

This type of method of detecting and quantifying an analyte present in a sample, sometimes in trace amounts, is of great interest to research or analysis laboratories, especially clinical or biological analysis laboratories.

However, for routine use, the methods must be able to be applied simultaneously to a large number of samples. Furthermore, for one and the same sample, it is often necessary to carry out several tests.

Therefore, in most cases, the manual protocols of routine analysis involve several reactions and successive manipulation steps. These multiple tests are carried out on samples in series, in very large centers in which several tens of thousands of samples—may be tested per day. Such multiple tests may therefore impose constraints and require relatively lengthy performance times. Additionally, the successive manipulations which they require may give rise to errors in the results.

The problem of the automation of this type of test therefore rapidly arises, and various devices have thus been devised in order to achieve automation, or, at the very least, a simplification of the successive steps indicated above.

These devices remain however for the most part relatively complex or adapted to the detection of a particular type of analyte (cell or molecule) or else only allow qualitative analyses to be carried out. Such devices are described in particular in the documents EP 0339277 and EP 0426729.

In particular, the document EP 339 277 describes a device for performing successive analytical reactions for dosing an analyte in a liquid assay sample involving analytical reactions between the analyte and analytical reagents which interact with the analyte to produce an analyte-dependent detectable response.

This device comprises a closed receptacle having a horizontal axis of rotation. This closed receptacle is delimited externally by a cylindrical wall and internally comprises two concentric spoon-shaped walls which define between themselves a sample inlet zone. Between said spoon-shaped walls and the cylindrical peripheral wall there are defined several reaction zones into which the specific analytical reagents are incorporated.

According to this document, the sample is introduced by an entry pathway into the inlet chamber defined between the spoon-shaped walls and opening toward the reaction zones. By pivoting said receptacle in a swinging movement about its horizontal axis, the liquid sample is transported by gravity into the reaction zones where it interacts with the reagents and then transported to an examination zone situated at the center of the receptacle.

Such a device is designed chiefly to avoid any centrifugation of the product when carrying out dosing.

The document JP HEI-5 215 750 also discloses a device for detecting and analyzing cellular populations, which comprises a horizontal circular dish mounted rotatably about a vertical axis. This open dish is covered with antibodies.

It is rotated about its vertical axis so that the sample introduced at its center is distributed under the action of a centrifugal force over said dish.

The subsequent washing steps are carried out in the same way by introducing the rinsing liquid at the center of the dish, the liquid being discharged toward the periphery of the dish during the rotation of the latter, while rinsing the surface on which the component to be dosed is fixed. In order to recover the rinsing liquid, there is provided a receptacle placed beneath the dish.

Finally, the document WO 94 25 159 discloses a device for the qualitative and/or quantitative dosing of a particular component in a sample of products, which comprises a substantially circular container mounted rotatably on a shaft for driving via a central housing, and in which test chambers are made which extend along radii of the container and which have a density gradient. In the central part of the container, there is provided an annular centrifugation chamber which is in communication with each test chamber.

This annular centrifugation chamber can be divided into two parts which communicate with each other via an upper opening.

The wall delimiting the first part of the centrifugation chamber is inclined so that the products are transferred from the first part to the second part by overflowing from the delimiting wall, via the communication orifice. Likewise, the wall delimiting the second part of the centrifugation chamber exhibits an inclined slope so that the mixture is transferred into each test chamber by overflowing via the communication orifice between the second part of the centrifugation chamber and said test chambers.

The slope of the wall delimiting the second part of the centrifugation chamber is greater than the slope of the wall delimiting the first part so that during centrifugation, the product passes firstly from the first part of the centrifugation chamber situated close to the axis of rotation of the container, to the second part of the centrifugation chamber before being transferred to the test chambers.

SUMMARY OF THE INVENTION

The invention proposes a novel arrangement of a dosing device which is of simple design and easy to use and which can be manipulated individually with a minimum number of manipulations so as to carry out dosing, allowing dosings to be carried out in proximity to the place of withdrawal of the product sample containing the particular component to be dosed, such a device exhibiting an optimized arrangement and furthermore making it possible to carry out assays in series from small quantities of samples.

More particularly, according to the invention, there is proposed a device for the qualitative and/or quantitative dosing of at least one particular component in a product sample by labeling and fixing, said device comprising a container and a cover which are assembled to form a closed receptacle.

This device is characterized in that said closed receptacle has a vertical axis, in that the container and the cover carry coaxial cylindrical walls which, while the container and cover are being assembled, position themselves pairwise one against the other thereby delimiting at least three concentric annular chambers inside the receptacle, namely from the axis an inlet chamber intended for receiving the sample and as appropriate allowing the labeling of the component, a chamber for fixing and reading said labeled component and a discharge chamber, in that the coaxial cylindrical walls forming separations between the successive annular chambers each comprise at least one opening, and in that the assembled cover and container are able to turn with respect to one another about the vertical axis and the openings of the coaxial cylindrical walls of the container and of the cover are placed at determined angular positions, in such a way that by displacement of one with respect to the other of the cylindrical walls of each pair, the openings of each pair of walls are able to be positioned opposite one another or in an angularly offset manner, so as to put into communication or isolate from one another the successive annular chambers.

According to a preferred arrangement of the device in accordance with the invention, said openings provided in the coaxial cylindrical walls of the container and of the cover are positioned in such a way that the openings of a pair of cylindrical walls are opposite one another so as to put into communication two successive annular chambers, the openings of the other pairs of cylindrical walls are positioned in an angularly offset manner so that the other annular chambers are isolated.

According to other advantageous characteristics of the device in accordance with the invention, on the cover and on the container if comprises means of indexed positioning of these latter. The cover comprises a nipple on the external face of one of these coaxial cylindrical walls which are situated outside the other cylindrical walls so as to form the external peripheral edge of the receptacle, said nipple forming a grip or a sill for turning the cover about the vertical axis with respect to the container. The device according to the invention comprises a central through-orifice isolated from the immediately adjacent annular chamber and intended to be threaded onto a vertical shaft for rotational driving for setting said receptacle into rotation.

In the bottom of the cover or in the bottom of the container, there may be provided an entry orifice to the inlet chamber.

According to a variant of the device in accordance with the invention, provision may be made for the receptacle to comprise several concentric fixing and reading chambers between the inlet chamber and the discharge chamber.

The device according to the invention exhibits an optimized ergonomic shape. More particularly, its receptacle exhibits the shape of a disk.

Advantageously, the container of the device according to the invention is made from a transparent material so as to allow reading of the labeled fixed components in the fixing and reading chamber through the walls of said receptacle. The cover may be opacified or be treated in such a way as to avoid parasitic radiations, it being possible for the reading to be performed with the aid of a CCD camera.

The device according to the present invention preferably comprises in the fixing chamber at least one receptor of the component to be dosed, said receptor being fixed in the chamber. It should be understood according to the present invention that the terms receptor and ligand will be used to designate in a generic manner two elements which are bound by strong interactions, and it can therefore relate equally to an antigen/antibody pair or to a nucleic acid/complementary nucleic acid pair or else to a true ligand and receptor or other strong interactions.

The techniques making it possible to fix proteins (antigens, antibodies for example) or nucleic acids on plastic or even glass surfaces are well known to the person skilled in the art, these dealing with technologies currently used in particular to fix components of this same type in the standard microtiter plates which are used for example in ELISA or else which may be adapted as a function of the type of polymer involved.

Preferably the receptor will be fixed on the bottom of the container, if possible in the form of a monolayer so as to allow easier reading. Indeed, when the means of reading is a CCD camera, the radiation will pass through the bottom of the container and will or will not be modified by the presence of a labeled component and will then be recovered after a second pass through the bottom of the container.

The technique involved is in a general manner akin to so-called sandwich immunological dosing processes, that is to say the element to be detected reacts with the receptor for example the antibody and is itself labeled by another element recognizing it, which carries either a physical label, that is to say particles, or else a chemical label for example with the aid of fluorescent elements or ones which may be rendered fluorescent.

In this regard, according to an advantageous characteristic of the invention, the labeling particles exhibit a sufficient diameter, preferably greater than or equal to around 100 times the diameter of the component(s) to be dosed and possess optical properties allowing their detection by counting.

The expression "possess optical properties" is understood to mean the fact that said particles are able to reflect all or some of a luminous radiation emitted by a detection system, heading for said particles.

Although it is possible to label the component before introducing it into the device, the labeling element capable of labeling the component to be dosed will preferably be placed in the inlet chamber, for example in unfixed dry form, this involving for example labeled antibodies recognizing one of the epitopes of the antigen to be dosed, another antibody being fixed in the fixing and labeling chamber.

In the device according to the present invention, the fixed receptor is chosen as indicated above from among:

- antibodies, antigens, complementary nucleic acid sequences,
- true receptors for specifically dosing components which are:
- antigens, antibodies, nucleic acid sequences, ligands of said receptors.

For the immunological dosings, use will preferably be made of an antigen or a labeled antibody to respectively dose the complementary element and another complementary element will be fixed in the fixing and reading chamber.

It is also possible to provide for multiple dosing making it possible to dose perhaps several antigens or several antibodies. To do this it is sufficient for the fixing and reading chamber to be divided into plurality of angular sectors on which mutually different receptors are fixed, each intended for fixing and reading a different labeled component. For this purpose, it may be particularly advantageous according to the invention for an angular sector of the fixing chamber to be left devoid of receptors so as to constitute a blank sector intended for carrying out an initialization reading of said device to zero it.

Reading may be carried out according to the invention by virtue of a CCD camera which may of course be controlled by a computerized device which will make it possible to reconstruct the dosing of each of the elements as a function of the readings which will be made on the various sectors.

According to a particularly advantageous characteristic of the device according to the invention, the CCD camera is able to count in a discretionary manner by emission/reception of a light signal, the number of labeled fixed components in each fixing and reading chamber, so as to obtain a digital detection signal.

This entails using particles or microspheres to label the component or components to be dosed in the sample, these particles preferably exhibiting a size greater than around 100 times the size of the sought-after molecules, and being capable of returning all or some of a luminous radiation emitted in their direction, reflected radiation constituting so many events which are captured by the CCD camera used and transmitted to a computerized tool adapted for expressing the detected events in terms of absolute number in real time.

The invention also proposes a process for the qualitative and/or quantitative dosing of at least one particular component in a product sample by labeling and fixing.

This process is characterized in that use is made of at least one device according to the invention which contains specific receptors for the component to be dosed, which are fixed in each fixing and reading chamber and in which process, a) the product sample containing the labeled component is placed in the inlet chamber isolated from the other annular chambers, b) the cover is turned with respect to the container in such a way as to put the inlet chamber into communication with each fixing and reading chamber, the discharge chamber being isolated from the other annular chambers, c) the device is rotated about its vertical axis in such a way as to disperse by centrifugation in each fixing and reading chamber the product sample containing the labeled component, the latter then binding by strong interaction to the fixed specific receptors in each fixing and reading chamber, d) the cover is turned with respect to the container in such a way as to put the fixing and reading chamber into communication with the discharge chamber, e) the device is rotated about its axis in such a way as to disperse by centrifugation the surplus sample into the discharge chamber, f) the inside of the device is rinsed with the aid of a rinsing liquid which is circulated by centrifugation through the various annular chambers of said device while reproducing the preceding steps b), c), d) and e) in such a way as to retain in each fixing and reading chamber only the labeled component bound by strong interaction to the fixed receptors, g) said labeled component is detected and dosed through the wall(s) of said device.

The process according to the invention can be automated and is "generic", it can be applied to the detection and to the counting of target substances, either of a molecular, particulate, vesicular or cellular nature.

The invention also proposes an apparatus for implementing the aforesaid process, characterized in that it comprises a vertical shaft for rotational driving on which are threaded devices according to the invention, means for maintaining said devices distanced from one another, means for the bidirectional rotational driving of said vertical drive shaft, means for injecting product samples and rinsing liquid into the inlet chambers of said devices threaded on the drive shaft, and means for turning the covers of the devices relative to the containers in such a way as to put the various successive annular chambers of these containers into communication or to isolate them and a means for reading the labeled fixed agents.

Thus, by virtue of the apparatus according to the invention, it is advantageously possible to carry out automatically, according to the process in accordance with the invention, using the device according to the invention, dosings of various components of one and the same sample, or one and the same component in particular in several samples of different products.

DESCRIPTION OF THE DRAWINGS

The description which follows in conjunction with the appended drawings, given by way of nonlimiting examples, will clearly elucidate that of which the invention consists and how it may be embodied.

In the appended drawings.

DESCRIPTION OF THE PREFERRED EMBODIMENT

Figure 1:
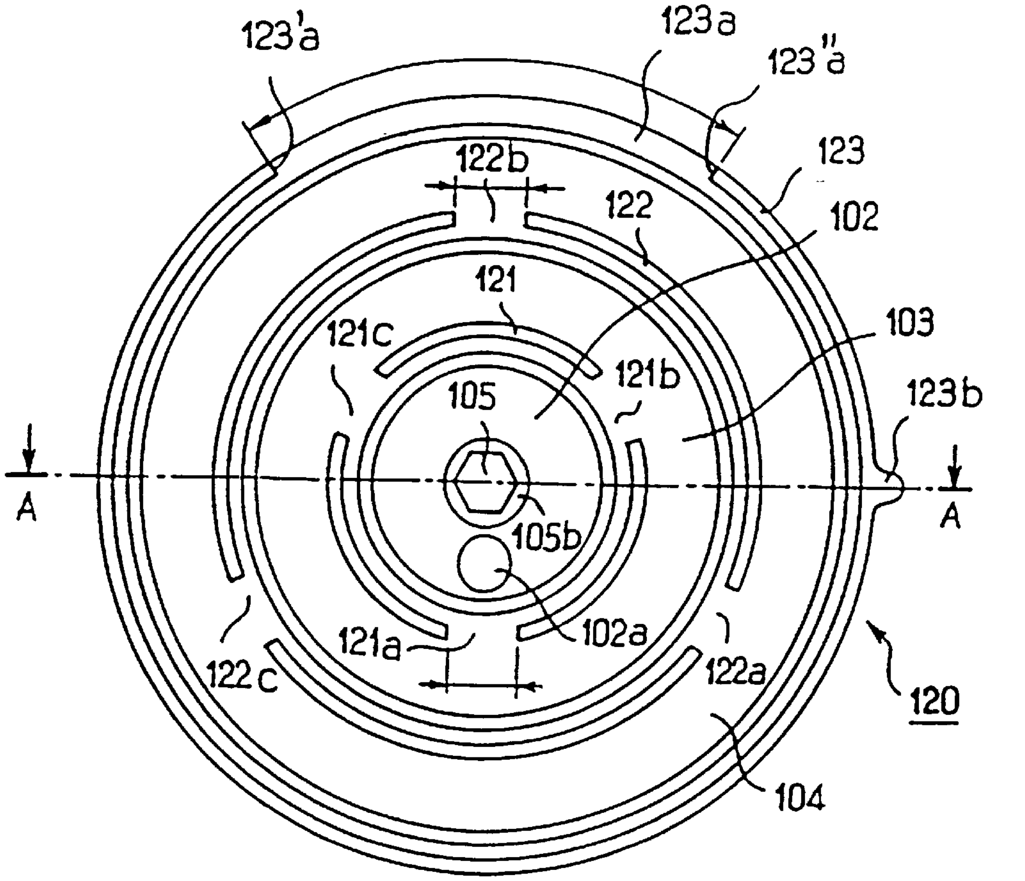
FIG. 1 is a top view of the cover of an embodiment of the device according to the invention.
Figure 2:
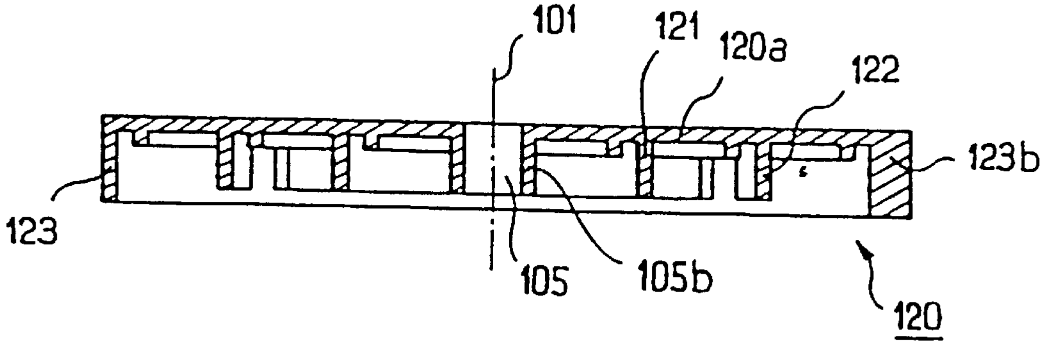
FIG. 2 is a sectional view along the plane A—A of FIG. 1.

Represented in FIGS. 1 to 4 as separate pieces is a device for the qualitative and/or quantitative dosing of at least one particular component in a product sample by labeling and fixing.

Such a device is used advantageously to carry out immunological dosing, detection of microorganisms, dosing of pollutants or else to reveal a particular nucleic acid sequence.

Such a device comprises a container 110 and a cover 120 which are intended to be assembled to form a closed receptacle.

As is represented in the figures, the container 110 and the cover 120 exhibit a circular general shape, with a central axis of symmetry 101, so that when they are assembled, said closed receptacle thus formed exhibits the shape of a disk with a vertical axis 101.

The container 110 and the cover 120 each exhibit a bottom 110*a*, 120*a*which carries coaxial cylindrical walls 111, 112, 113; 121, 122, 123 (here three in number). While said container 110 and said cover 120 are being assembled these coaxial cylindrical walls position themselves pairwise one against the other thereby delimiting here three concentric annular chambers 102, 103, 104 inside the closed receptacle.

Starting from the axis and proceeding toward the outside, said cylindrical walls delimit firstly an inlet chamber 102 intended for receiving the product sample and as appropriate allowing the labeling of the component to be dosed, for example an antibody labeled with a particle in dry form, a chamber for fixing and for reading said labeled component 103, comprising for example an antibody fixed at the bottom of the container, and a discharge chamber 104.

According to the embodiment represented, the cover exhibits a diameter slightly greater than the diameter of the container, so that the cover positions itself on the container. The cylindrical wall 123 of the cover 120, which wall is situated outside the other coaxial cylindrical walls 121, 122, then forms according to the embodiment represented the exterior peripheral edge of said receptacle. The coaxial cylindrical walls 111, 112, 113 of the container 110 are intended to position themselves against the interior faces of the coaxial cylindrical walls 121, 122, 123 of the cover 120.

The coaxial cylindrical interior walls 111, 112 and 121, 122 of the container 110 and of the cover 120 which form separations between the successive annular chambers 102, 103, 104 each comprise at least one opening 111*a*, 112*a* and 121*a*, 122*a*.

Here each of these coaxial cylindrical walls 111, 112; 121, 122 comprises three openings 111*a*, 111*b*, 111*c*, 112*a*, 112*b*, 112*c*; 121*a*, 121*b*, 121*c*; 122*a*, 122*b*, 122*c* regularly distributed over the outline of each wall while being offset pairwise by around 120 degrees.

In the exemplary embodiment represented, the openings of the coaxial cylindrical walls of the container 110 and of the cover 120 are formed by notches.

Said openings of the coaxial cylindrical walls of the container 110 and of the cover 120 are placed at determined angular positions, and the assembled cover 120 and container 110 are able to turn with respect to each other about the vertical axis 101 in such a way that by displacement of one with respect to the other of the cylindrical walls of each pair forming a separation of successive annular chambers, said openings of each pair of the walls are able to be positioned opposite one another or in an angularly offset manner, so as to put into communication or isolate from one another said successive annular chambers.

According to the typical case, the openings 111*a*, 111*b*, 111*c* made in the cylindrical wall 111 of the container 110 are disposed respectively facing the openings 112*a*, 112*b*, 112*c* made in the cylindrical wall 112 of the container 110. Stated otherwise, each opening 111*a*, 111*b*, 111*c* made in the internal cylindrical wall 111 of the container 110 is positioned facing a corresponding opening 112*a*, 112*b*, 112*c* made in the coaxial cylindrical wall 112 positioned-outside said wall 111.

On the other hand, the openings 121*a*, 121*b*, 121*c* formed in the cylindrical wall 121 of the cover 120 are positioned offset with respect to the openings 122*a*, 122*b*, 122*c* made in the coaxial cylindrical wall 122 of the cover 120, which wall is situated outside said cylindrical wall 121, with an angular offset of around 60 degrees, so that the openings made in one wall are not positioned facing the openings formed in the other successive coaxial wall of the cover.

Thus, with such an arrangement, when the cover 120 is assembled with the container 110, it is positioned with respect to the latter in such a way that the openings of one pair of cylindrical walls are facing one another so as to put two successive annular chambers into communication, the openings of the other pair of cylindrical walls being positioned in an angularly offset manner so that the other two successive annular chambers are isolated from one another.

Furthermore, as shown by FIGS. 1 to 4, the cover 120 and the container 110 are provided with means of indexed positioning.

According to the embodiment represented, said means of indexed positioning of the cover 120 and of the container 110, comprise on the one hand, an opening 123*a* extending over an angular sector of the cylindrical wall 123 of the cover 120 which is situated outside the other coaxial cylindrical walls and forms the external peripheral edge of the receptacle, and on the other hand, a nipple 113*a* extending radially while projecting from the cylindrical wall 113 of the container 110 intended to be positioned against the external cylindrical wall 123 of the cover 120, said nipple 113*a* being able to engage in said opening 123*a* of the external wall 123 of the cover 120 and to navigate in this opening 123*a* during relative rotation of the cover 120 and of the container 110, in such a way as to come into abutment against the two end lateral edges 123'*a*, 123"*a* of this opening 123*a*.

Here, the opening 123*a* created in the external wall 123 of the cover 120 is embodied by a notch which extends over around 70 degrees.

The two abutting positions of the nipple 113*a* in the opening 123*a* correspond to two determined relative positions of the cover 120 and of the container 110.

A first abutting position of the nipple 113*a* against the end edge 123'*a* of said opening 123*a*, here corresponds to the putting of the inlet chamber for the product sample 102 into communication with the chamber for fixing and reading the labeled component 103, the discharge chamber 104 being isolated from the other chambers.

The second abutting position of the nipple 113*a* against the other end edge 123"*a* of said opening 123 here corresponds to the putting of the fixing and reading chamber 103 into communication with the discharge chamber 104 and to the isolating of the inlet chamber 102 from the other chambers.

So as to facilitate the relative rotation of the cover 120 and of the container 110, the cover 120 comprises a nipple 123*b* extending radially while projecting from the external face of the cylindrical wall 123 situated outside the other cylindrical walls, said nipple 123*b* forming a grip or a sill for turning the cover 120 about the vertical axis 101 with respect to the container 110.

The container 110 and the cover 120 are each provided with a central through-orifice 105 isolated from the immediately adjacent annular chamber, here the inlet chamber 102, by a coaxial cylindrical wall 105*a*, 105*b*. When the cover is assembled with the container the walls 105*a* and 105*b* of the container 110 and of the cover 120 will position themselves one against the other and the closed receptacle thus formed comprises a central through-orifice, isolated by the two cylindrical walls 105*a*, 105*b* positioned one against the other, from the immediately adjacent annular chamber 102.

This central through-orifice 105 is intended for being threaded onto a vertical shaft for rotational driving for setting said receptacle into rotation. The orifice 105 here exhibits a diameter of around 4 mm.

The openings created in the coaxial cylindrical walls of the container 110 and of the cover 105 for putting the annular chambers of the receptacle into communication exhibit a width of around 5 mm.

As shown more particularly by FIG. 1, in its bottom 120*a* the cover 120 comprises an orifice 102*a* emerging into the inlet chamber 102. It is placed adjacent to the through-orifice 105 since the inlet chamber is immediately adjacent to said through-orifice 105.

Of course, provision could be made for this entry orifice to the inlet chamber to be made according to a variant (not represented) in the bottom 110*a* of the container 110.

The container 110 is made from a transparent material in such a way as to allow the reading of the labeled fixed components in each fixing and reading chamber, through the bottom wall of said container for example with the aid of a CCD camera, by transmission and reflection of radiation.

The cover can then be opacified, i.e. treated so as to avoid spurious radiations.

Advantageously, the container and the cover are made by molding a plastic, the coaxial cylindrical walls being formed together with said cover.

Any plastic material conventionally used for "coating" molecules can be used to embody the device according to the invention. Use will be made for example of polystyrene, or preferably, a ZYLAR (registered trademark) plastic, such a plastic exhibiting a very high fixing capacity in terms of "coating".

According to a variant of said dosing device, there may advantageously be provision for the fixing and reading chamber 103 to be divided into a plurality of angular sectors on which mutually different receptors are fixed, each intended for the fixing and for the reading of a different labeled component. According to this variant, it may be particularly advantageous to provide for an angular sector of the fixing chamber to be devoid of fixed receptors so as to constitute a blank sector on which it will subsequently be possible to carry out reading to determine the initialization zero of the device.

According to another variant there may also be provision for the receptacle to comprise between the inlet chamber and the discharge chamber several other concentric successive fixing and reading chambers for fixing different labeled components.

Figure 3:
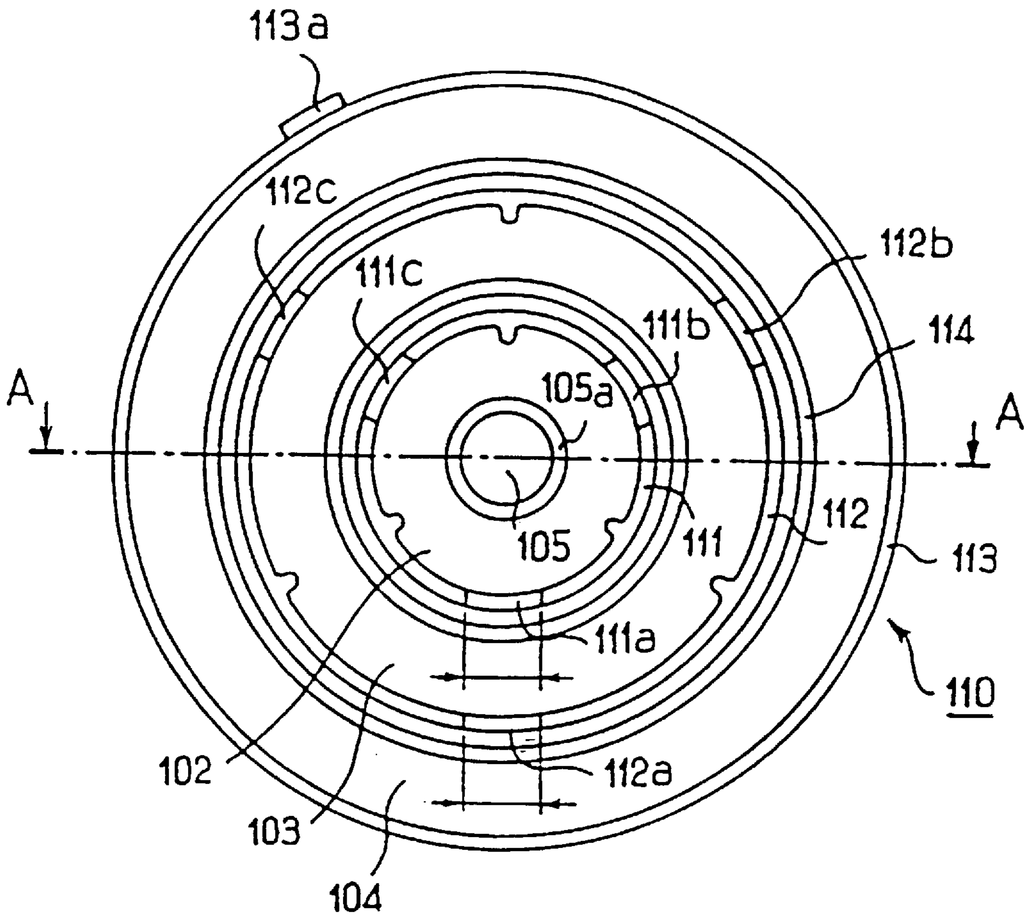
FIG. 3 is a top view of the container of the embodiment of FIG. 1 of the device according to the invention.

The dosing device constructed by assembling the container 110 and the cover 120 such as they are represented in FIGS. 1 and 3 allows the implementation of a process for the qualitative and/or quantitative dosing of at least one particular component in a product sample by fixing labeling. This process will be described hereinbelow.

According to this process, use is made of at least one device of the type described above with the two elements, container and cover, such as they are represented in FIGS. 1 and 3, assembled to form the closed receptacle, which contains specific receptors for the component to be dosed, which are fixed in the fixing and reading chamber.

During a first step a), the product sample containing the labeled component to be dosed is then placed in the inlet chamber isolated from the other annular chambers of said receptacle.

Then during a step b), the cover is turned with respect to the container in such a way as to put the inlet chamber into communication with the fixing and reading chamber, the discharge chamber being isolated from the other annular chambers.

Then during a step c), the device is rotated about its vertical axis in such a way as to disperse by centrifugation in the fixing and reading chamber the product sample containing the labeled component to be dosed, the latter then binding by strong interaction with the fixed specific receptors in the fixing and reading chamber.

It is noteworthy to stress that the rotation of the device allows the transfer of the product sample from the inlet chamber to the fixing and reading chamber, but also the agitation of the sample inside this chamber so as to allow the labeled component to bind with the fixed receptors.

During a next step d), the cover is turned with respect to the container in such a way as to put the fixing and reading chamber into communication with the discharge chamber, and then during a step e), the device is rotated about its axis in such a way as to disperse by centrifugation the surplus sample into the discharge chamber.

Figure 4:
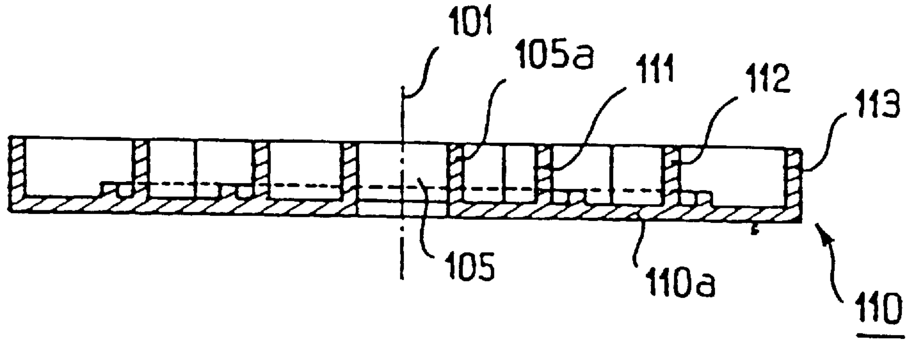
FIG. 4 is a sectional view along the plane A—A of FIG. 3.

It should be pointed out that for this purpose, as shown by FIGS. 3 and 4, there is provided in the bottom 110*a* of the container 110 of the device, a circular rib 114 in proximity to the interior cylindrical wall 112 forming the separation between the fixing and reading chamber, and the discharge chamber, this circular rib 114 forming a non-return lip in respect of the surplus sample discharged by centrifugation in said discharge chamber, or else in respect of the rinsing liquid recovered in this chamber as will be described hereinbelow.

During a step f), the inside of the device is rinsed several times with the aid of a rinsing liquid which is circulated by centrifugation through the various annular chambers of said device while reproducing the preceding steps b), c), d) and e) so as to eliminate the other components of said product which may be attached by adsorption to the internal walls of the device or else bound by weak interaction (such as adsorption) to the specific receptors fixed in the fixing and reading chamber.

Thus, only the labeled component, bound by strong interaction to the fixed receptors in said chamber is retained in the fixing and reading chamber after rinsing.

It is then possible in step f) to detect and dose through the wall(s) of said device the labeled component bound to the fixed receptors in such a way as to perform qualitative and/or quantitative dosing of this labeled component.

This detection can be carried out advantageously according to the process in accordance with the invention with the aid of a CCD camera. To do this, the labeling of the component to be dosed must be carried out physically or chemically with the aid for example of fluorescent microspheres or ones which are rendered fluorescent.

The reading of the labeled fixed agents may be performed along radii of the fixing and reading chamber.

More particularly, according to the process in accordance with the invention with the aid of a CCD camera, the number of labeled fixed components in each fixing and reading chamber is counted. This is possible using, as labeling elements capable of labeling the component to be dosed, particles or microspheres preferably around 100 times larger than the sought-after molecules, and conjugated with the revealing antibody or antigen. For better resolution by the CCD camera, particles whose diameter is 2 $\mu$m are favored.

These microspheres are such that they reflect all or some of the radiation which they receive. They can consist of latex or any other material allowing their detection and their counting.

Thus, the CCD camera captures a determined number of events corresponding to an absolute number of fixed components to be dosed.

The CCD camera is linked to software which outputs a digital detection signal. Such a vision-based system thus provides a real-time count of from a few units to 100,000 microspheres per $mm^2$, with subtraction of background noise with the aid of a reference surface and appropriate dialgorithms. It also possesses discriminating power insofar as it can recognize and discard the heterogeneous images liable to falsify the analysis of the data.

Figure 5:
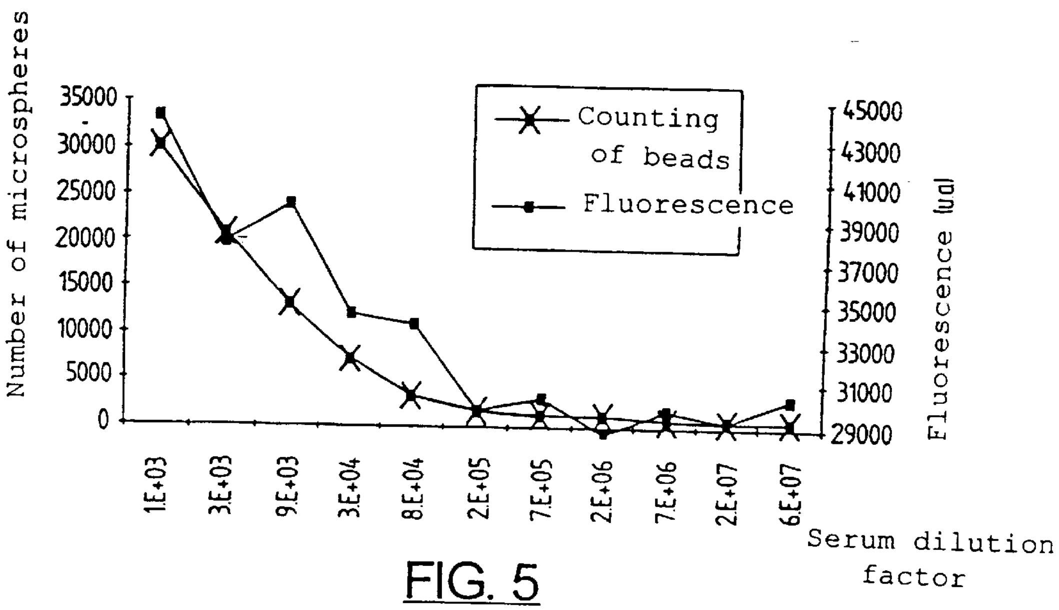
FIG. 5 presents two detection curves for a given component in a serum, by fluorescence and by counting of labeling microspheres according to the invention.
Figure 6:
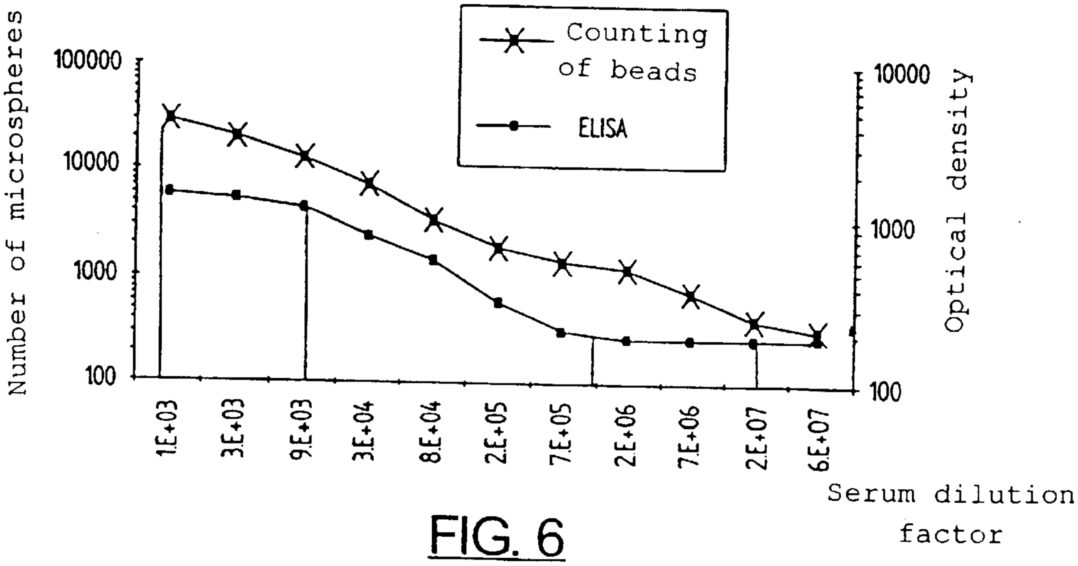
FIG. 6 presents two detection curves for a given component in a serum, by the ELISA method and by counting of microspheres according to the invention.

FIGS. 5 and 6 show curves of results obtained with the aforesaid method of detection by counting according to the invention and more conventional detection methods of the fluorescence-based or ELISA type, for a given component to be dosed in a given serum.

The curves of FIGS. 5 and 6 demonstrate on the one hand that there is indeed a correlation between the counting of the microspheres and the concentration of the component to be dosed, and on the other hand that the method of counting microspheres according to the invention is more accurate than the so-called conventional detection methods. In particular, dosing by counting of microspheres offers a dynamic range of more than 4Log as against 2Log for the ELISA method. This is particularly advantageous since one thereby considerably increases the limit of detection. The results obtained with strong dilutions of the sample thus show that the method exhibits a sensitivity 2Log greater than that of ELISA. The results obtained on weak dilutions of the sample also show that the method still makes it possible to carry out dosings at analyte concentrations corresponding to a saturation threshold in ELISA. This can therefore advantageously make it possible to avoid or to decrease any effects of dilution on certain components of sample to be tested.

According to the aforesaid process, the labeling of each particular component of the sample can be carried out outside before introducing said sample into said inlet chamber of the device.

As a variant, the labeling of each particular component to be dosed of the product sample can be carried out directly in the inlet and labeling chamber, in a first step by introducing a specific labeled receptor for each component to be dosed, in unfixed dry form, then in a second step by introducing the product sample into said isolated inlet chamber so that the labeled receptor will bind by strong interaction to the corresponding component contained in said product sample.

Of course, this process described with the aid of a device and such as represented in FIGS. 1 to 4, can be carried out with the aid of a plurality of devices of this type, so as to simultaneously dose one and the same particular component in a plurality of different samples or else to dose various particular components in one and the same product sample.

For this purpose, there is advantageously provided according to the invention an apparatus for implementing this process using a plurality of devices of the type of that represented in FIGS. 1 to 4, which comprises a vertical shaft for rotational driving on which are threaded said dosing devices, means for maintaining said devices distanced from one another, means for the bidirectional rotational driving of said vertical drive shaft so as to carry out the rotational centrifugation of said devices, means for injecting product samples and the rinsing liquid into the inlet chambers of devices threaded on the drive shaft, and means for turning the covers of the devices relative to the containers in such a way as to put the-various successive annular chambers of said devices into communication or to isolate them, and a means of reading the labeled fixed agents.

The invention is in no way limited to the embodiments described and represented, but the person skilled in the art will know how to vary it in any manner in accordance with the spirit thereof.

What is claimed is:

1. A device for qualitative and/or quantitative dosing of at least one particular component in a product sample by labeling and fixing, said device comprising a container and a cover which are connected to form a closed receptacle, wherein said closed receptacle has a vertical axis, the container and the cover carrying coaxial cylindrical walls which, while the container and cover are being connected, position themselves pairwise one against another thereby delimiting at least three concentric annular chambers inside the receptacle, namely from the axis an inlet chamber for receiving the sample and allowing labeling of the component, a chamber for fixing and reading said labeled component, and a discharge chamber, the coaxial cylindrical walls forming separations between successive annular chambers each having at least one opening, and the connected cover and container being relatively rotatable about the vertical axis, and the openings of the coaxial cylindrical walls of the container and of the cover being placed at predetermined angular positions in such a way that by displacement of one with respect to the other of the cylindrical walls of each pair, the openings of each pair of walls are able to be positioned opposite one another or in an angularly offset manner, so as to put into communication or isolate from one another the successive annular chambers.

2. The device according to claim 1, wherein said openings provided in the coaxial cylindrical walls of the container and of the cover are positioned in such a way that when openings of a pair of cylindrical walls are opposite one another so as to put into communication two successive annular chambers, openings of other pairs of cylindrical walls are positioned in an angularly offset manner so that other annular chambers are isolated.

3. The device according to claim 1, wherein at least one of the cover and the container comprises index means for placement of the cover at a predetermined position relative to the container.

4. The device according to claim 3, wherein said cover comprises an external cylindrical wall with an opening extending over an angular sector thereof bounded by a first lateral edge and a second lateral edge, and said container comprises a nipple extending radially into said opening of the external cylindrical wall of the cover, during relative rotation of the cover and of the container, in such a way as to come into abutment against one of said two end lateral edges when said cover and container are in one of two predetermined relative positions of the cover and of the container, and against the other of said two end lateral edges when said cover and container are in the other of said two predetermined relative positions of the cover and of the container.

5. The device according to claim 4, wherein a first abutting position of the nipple in said opening corresponds to the sample inlet chamber being in communication with the chamber for fixing and reading the labeled component, the discharge chamber being isolated from the other chambers, and a second abutting position of the nipple in said opening corresponds to the the fixing and reading chamber being in communication with the discharge chamber and to the isolating of the inlet chamber.

6. The device according to claim 1, wherein the cover comprises a nipple on an external face of one of its coaxial cylindrical walls which is situated outside the other cylindrical walls so as to form an external peripheral edge of the receptacle, said nipple forming a grip or a sill for turning the cover about the vertical axis with respect to the container.

7. The device according to claim 1, wherein the receptacle comprises a central through-orifice isolated from an immediately adjacent annular chamber for being threaded onto a vertical shaft for rotational driving for setting said receptacle into rotation.

8. The device according to claim 1, wherein in a bottom of the cover or in a bottom of the container, there is an entry orifice to the inlet chamber.

9. The device according to claim 1, wherein between the inlet chamber and the discharge chamber the receptacle comprises a plurality of concentric fixing and reading chambers.

10. The device according to claim 1, wherein said coaxial cylindrical walls forming separations between the successive annular chambers each comprise three openings regularly distributed over their circumference.

11. The device according to claim 1, wherein the receptacle is in the shape of a disk.

12. The device according to claim 1, wherein the container is made from a transparent material so as to allow reading of the labeled fixed components in the fixing and reading chamber through the walls of said receptacle.

13. The device according to claim 1, comprising plastic.

14. The device according to claim 1, wherein said chamber for fixing and reading has a wall on which at least one receptor of the component to be dosed is fixed.

15. The device according to claim 14, wherein said wall is a bottom wall of the container.

16. The device according to claim 1, wherein the inlet chamber comprises a labeling element for labeling the component to be dosed.

17. The device according to claim 14, wherein the receptor is chosen from the group consisting of:

antibodies, antigens, complementary nucleic acid sequences, true receptors for respectively dosing components which are:

antigens, antibodies, and nucleic acid sequences, ligands of the receptors.

18. The device according to claim 1, wherein the chamber for fixing and reading is divided into a plurality of angular sectors on which are fixed mutually different receptors, each for fixing and for reading a different labeled component.

19. The device according to claim 18, wherein an angular sector of the fixing chamber is left devoid of receptors so as to constitute a blank sector for carrying out an initialization reading of said device.

20. The device according to claim 16, wherein the labeling is performed by physical or chemical means.

21. The device according to claim 20, wherein the labeling is performed with fluorescent particles and/or elements.

22. The device according to claim 21, wherein the particles have a diameter greater than or equal to around 100 times the diameter of the component(s) to be dosed and are reflective for allowing their detection by counting.

23. The device according to claim 21, wherein the particles have a diameter of 2 $\mu$m.

24. The device according to claim 16, wherein the labeling element consists of a labeled antibody or a labeled antigen, or a labeled nucleic acid sequence or a labeled receptor element.

25. The device according to claim 1, wherein the cover avoids parasitic radiations and further comprising a CCD camera for performing the reading.

26. The device according to claim 25, wherein the CCD camera counts, by emission/reception of a light signal, the number of labeled fixed components in each fixing and reading chamber, so as to obtain a digital detection signal.

27. A process for qualitative and/or quantitative dosing of at least one particular component in a product sample by labeling and fixing, wherein use is made of at least one device having a container, a cover mounted on the container to form a closed receptacle with a vertical axis and a plurality of pairs of coaxial apertured cylindrical walls defining an inlet chamber, a fixing and reading chamber, and a discharge chamber, the walls being relatively rotatable for selectively enabling and preventing communication between the chambers, said device containing specific receptors for the component to be dosed, which are fixed in each fixing and reading chamber and in which process, a) the product sample containing the labeled component is placed in the inlet chamber isolated from the other annular chambers, b) the cover is turned with respect to the container in such a way as to put the inlet chamber into communication with the fixing and reading chamber, the discharge chamber being isolated from the other annular chambers, c) the device is rotated about its vertical axis in such a way as to disperse by centrifugation in each fixing and reading chamber the product sample containing the labeled component, the labeled component then binding by strong interaction to the fixed specific receptors in each fixing and reading chamber, d) the cover is turned with respect to the container in such a way as to put the fixing and reading chamber into communication with the discharge chamber, e) the device is rotated about its axis in such a way as to disperse by centrifugation a surplus sample into the discharge chamber, f) the device is rinsed with a rinsing liquid which is circulated by centrifugation through the various annular chambers of said device while reproducing the preceding steps b), c), d) and e) in such a way as to retain in the fixing and reading chamber only the labeled component bound by strong interaction to the fixed receptors, g) said labeled component is detected and dosed through the wall(s) of said devices.

28. The process according to claim 27, wherein the labeling of each particular component to be dosed of the product sample is carried out before introducing the product sample into the inlet chamber of the device.

29. The process according to claim 27, wherein the labeling of each component to be dosed of the product sample is carried out in the inlet and labeling chamber by previously introducing into the product sample a specific labeling element for each component to be dosed, then by introducing the product sample into said isolated inlet chamber so that the labeling element will bind by strong interaction to a corresponding component contained in said product sample.

30. The process according to claim 27, wherein a reading operation allowing the detection of the labeled fixed component in the fixing and reading chamber is carried out with a CCD camera.

31. The process according to claim 30, wherein the CCD camera carries out a discretionary counting by emission/reception of a light signal of the labeled fixed components in each fixing and reading chamber, so as to obtain a digital detection signal.

32. The process according to claim 27, wherein a reading of the labeled fixed agents is performed along radii of the fixing and reading chamber.

* * * * *